United States Patent [19]

Jeong et al.

[11] 4,244,940
[45] Jan. 13, 1981

[54] SINGLE-INCUBATION TWO-SITE IMMUNOASSAY

[75] Inventors: Henry J. Jeong; Judith I. Blakemore, both of Benicia; Nathan Lewin, Corte Madera, all of Calif.

[73] Assignee: BIO-RAD Laboratories, Inc., Richmond, Calif.

[21] Appl. No.: 939,577

[22] Filed: Sep. 5, 1978

[51] Int. Cl.³ .................... G01N 33/48; A61K 43/00; B01T 1/00
[52] U.S. Cl. ...................... 424/1; 23/230 B; 422/61; 424/12
[58] Field of Search .................... 424/1, 12; 23/230 B; 422/61

[56] References Cited

U.S. PATENT DOCUMENTS

| | | | |
|---|---|---|---|
| 3,555,143 | 1/1971 | Axen et al. | 424/1 |
| 3,853,987 | 12/1974 | Dreyer | 424/1 |
| 3,995,019 | 11/1976 | Jerome | 424/1.5 |
| 4,017,597 | 4/1977 | Reynolds | 424/1.5 |
| 4,034,073 | 7/1977 | Weetalc | 424/1 |
| 4,088,746 | 5/1978 | Blakemore et al. | 424/1 |

OTHER PUBLICATIONS

Abraham, Ed, Handbook of Radioimmuno Assay, Marcel Dekker, Inc., N.Y., 1977, pp. 131–134.
Radioimmuno Assay and Related Procedures in Medicine, International Atomic Energy Agency, Vienna, 1974, pp. 131–147, 149–164.
Woodhead et al., Br. Med. Bull., vol. 30, No. 1, 1974, pp. 44–49.

*Primary Examiner*—Benjamin R. Padgett
*Assistant Examiner*—Christine M. Nucker
*Attorney, Agent, or Firm*—Townsend and Townsend

[57] ABSTRACT

This invention provides a two-site immunoassay method for a ligand utilizing a single incubation. The multivalent ligand, labeled receptor for the ligand and unlabeled receptor for the ligand covalently bound to a solid-phase support are incubated as a substantially stable suspension to produce a solid and liquid phase. The solid and liquid phases are separated from each other and the labeled receptor in either phase is quantitated.

The method may be used to assay for human thyroid stimulating hormone using purified, radioactively labeled antibodies and unlabeled antibodies covalently bound to hydrolyzed polyacrylamide particles.

20 Claims, 1 Drawing Figure

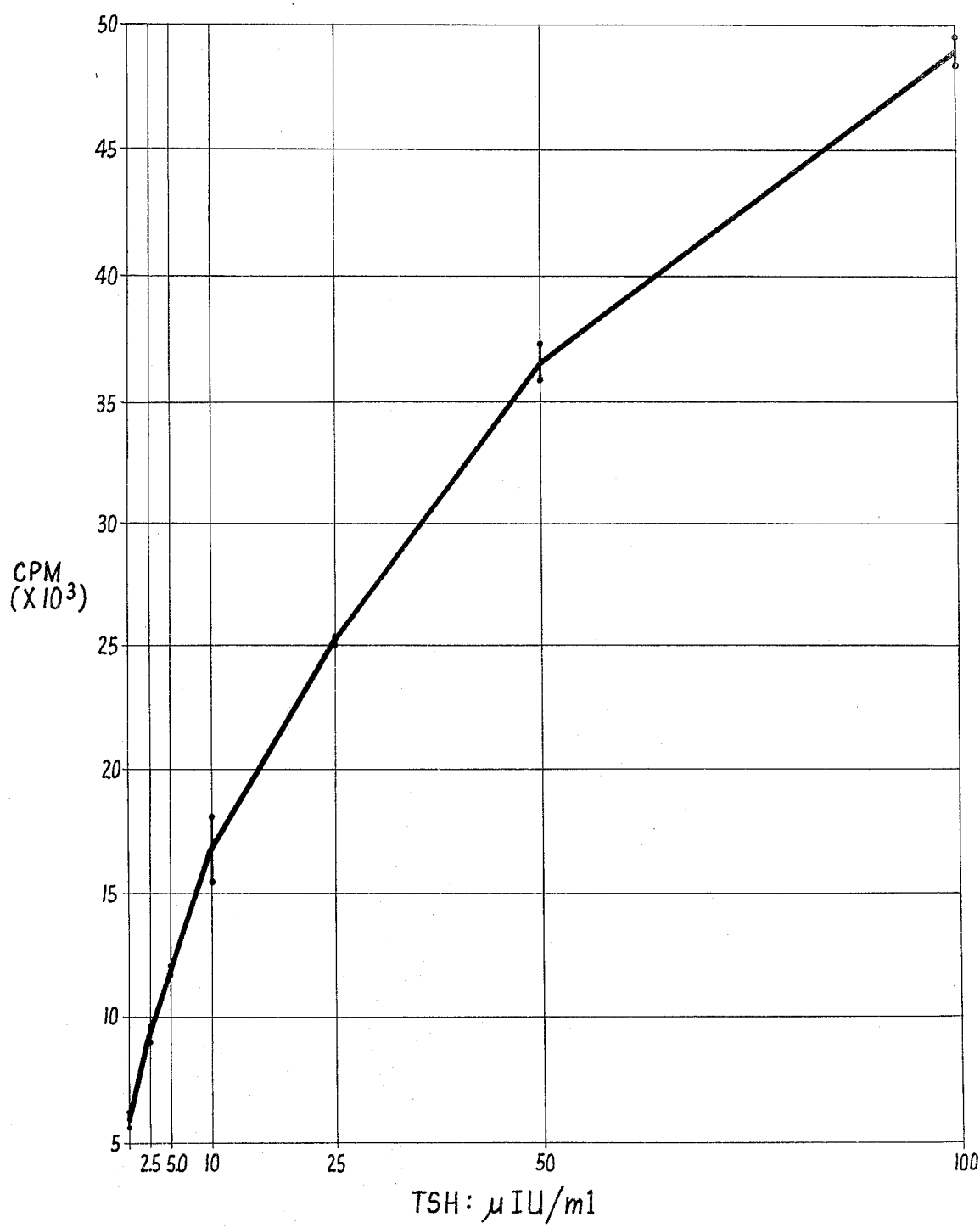

SINGLE-INCUBATION TWO-SITE IMMUNOASSAY

BACKGROUND OF THE INVENTION

1. Field of the Invention

This invention relates to a novel method for a two-site immunoassay.

2. Description of the Prior Art

Two-site immunoradiometric assays for antigens which can bind to at least two antibodies are known. Those known two-site immunoradiometric assays involve a first incubation of unlabeled antibody coupled to an insoluble matrix with the fluid containing the antigen having more than one antigenic determinant, followed by a second incubation with a labeled antibody. Woodhead, Addison and Hales, *Br. Med. Bull.*, Vol. 39, No. 1, 44–49 (1974); Abraham (ed.), *Handbook of Radioimmunoassay*, Ch. 4 (Marcel Dekker, Inc., 1977).

Such two-site immunoradiometric assays are discussed in *Radioimmunoassay And Related Procedures In Medicine*, Vol. 1, 131–47, 149–64 (International Atomic Energy Agency, Vienna 1974).

Corning Medical Diagnostics has marketed an assay for determination of human thyroid stimulating hormone (hereinafter referred to as "TSH"). See Corning, *TSH ($^{125}I$) Radioimmunoassay Test System (March, 1977)*. In that assay as described by Corning, the radioactive, $^{125}I$ antibody, specific for TSH, is added to a known amount of TSH standard or to a patient serum sample. The radioactive, $^{125}I$ antibody will bind to any TSH present and form a labeled complex. After a first incubation of equilibration period, another antibody, also raised against TSH, is added to the reaction mixture. This antibody has been covalently bonded to microscopic glass particles and serves to bind the labeled complex formed in the first step. After binding separation can occur by simple centrifugation. The precipitated complex is counted for $^{125}I$ radioactivity. A standard curve is constructed in which radioactivity bound to glass is plotted against TSH concentration. The counts bound in the presence of unknown patient samples are compared to the standard curve and the appropriate TSH concentration is determined by interpolation.

Corning also markets an assay for the determination of human thyroxine-binding globulin ("TBG"). See Corning, *TBG $^{125}I$ Radioimmunoassay Test System (December, 1977)*. In that assay, an immobilized antibody specific for TBG is added to a known amount of TBG standard or to a patient serum sample. After vortexing, radioactive $^{125}I$ labeled thyroxine ("$^{125}I$ T4") is added to the reaction mixture. According to Corning, the $^{125}I$ T4 will then partition between the binding sites on TBG and bovine serum albumin molecules present in the buffer. The TBG can thus become bound both to the immobilized antibody and to the $^{125}I$ T4.

The use of antibodies covalently bound to a solid-phase in radioimmunoassays for proteins and polypeptides is shown by U.S. Pat. No. 3,555,143, issued Jan. 12, 1971, to Axen and Wide. Pharmacia has applied that method in a commercial radioimmunoassay for TSH. In this procedure, the antibody is covalently bound to a polydextran. The sample to be determined and the solid-phase antibody are incubated at room temperature for 18–24 hours followed by addition of radioactively labeled TSH and further incubation with agitation for 18–24 hours. The solid phase is separated, washed three times and its radioactivity measured.

The patent application by Monthony et al. Ser. No. 621,197, filed Oct. 9, 1975, describes an immunofluorescent assay method in which the immune reactants are covalently bound to water insoluble hydrophilic polymeric particles of about 0.1–10 microns in size. The solid phase antibody is mixed with the sample containing antigen (or hapten) to be determined and corresponding antigen (or hapten) which has been fluorescently labeled, so as to bind a quantity of labeled and unlabeled antigen. The solid phase is separated and the fluorescence measured by optical spectroscopy, the concentration of the unknown immune reactant being a function of the value of the fluorescence. This application also describes a two-site immunoassay method in which an excess of solid phase antibody is first reacted with the sample containing antigen (or hapten) to be determined, and the complex is subsequently reacted with an excess of fluorescently labeled antibody.

SUMMARY OF THE INVENTION

The present invention in an improved two-site immunoassay method in which the sample containing the multivalent ligand to be determined, a labeled receptor for said ligand, and an unlabeled receptor for said ligand covalently bound to a solid-phase support (hereinafter referred to as "solid-phase receptor") are brought together in an aqueous medium to form a substantially stable suspension and in a single incubation mode or step to produce a two-phase system, wherein the solid phase contains the solid-phase receptor, a portion of which has become bound to ligand which in turn has become bound to a portion of the labeled receptor, and the liquid phase contains the unbound portion of the labeled receptor. The solid and liquid phases are separated and either phase analyzed for the labeled receptor, the concentration of which is a function of the concentration of ligand in the sample.

A two-site immunoassay employing a single incubation mode or step provides a significant advantage over assay procedures involving more than one incubation by simplifying, shortening, and rendering more convenient the performance of the assay. This improvement in assay procedure is accomplished while maintaining acceptable assay characteristics such as precision, specificity, and stability, and in addition, is less subject to errors in timing, additions, and other manipulations.

The novel two-site immunoassay of this invention can be applied to any ligand which can simultaneously become bound by two receptors. This group of ligands includes, but is not limited to placental, pituitary, calcium regulating, and adrenal medullary polypeptide hormones, protein and protein fragments; immunoglobulins (antibodies) of various classes; viral, bacterial, and protozoal organisms or particles; enzymes; and tumor-associated antigens. In a preferred example, an assay for human thyroid stimulating hormone is described.

This assay method utilizes a receptor for the ligand, which is any substance which binds the ligand with acceptable specificity and affinity. Accordingly, the receptor may be, for example, an antibody against the ligand. In a preferred example, antibodies are used as the receptor.

The labeled receptor may be labeled with any of a number of known tracers, including, for example, radioactive tags, such as iodine 125, or fluorescent labels. In a preferred example, radioactively labeled antibodies are employed.

An important component of this assay is the solid-phase support for unlabeled receptor which can form substantially stable suspensions in aqueous media, can be covalently bound to the unlabeled receptor, can be handled conveniently during manipulations such as pipetting and centrifuging, and exhibits low non-specific adsorption properties, or can be treated so that it exhibits such adsorption properties. The suspendability of the solid-phase support on which the unlabeled receptor is immobilized allows for the addition of an excess of solid-phase receptor, which binds the ligand in the sample, and yet permits further participation of the solid phase receptor-ligand complex in reactions with the labeled receptor. A suitable solid-phase support is derivatized polyacrylamide particles in a size range of 0.10 to 10 microns, which provides a substantially stable suspension during the single incubation period.

A preferred embodiment of this two-site immunoassay having a single incubation mode provides high specificity for TSH by using highly purified antibodies. The hormones TSH, HCG, FSH, and LH are each composed of similar alpha and distinct beta polypeptide chains. The hormones FSH, LH, and HCG may interfere with the assay for TSH due to the cross reactivity of the antibodies to those hormones. Improved specificity for TSH of this assay is achieved by a two step purification procedure for the labeled antibody and, if needed, purification of the unlabeled antibody to obtain antibodies of high affinity for TSH and low affinity for other hormones, for example HCG. Prepurification of receptor by these means constitutes an approach in dealing with inherent cross-reactivity due to common antigenic determinants in various subclasses of ligands and constitutes an improvement over prior art. In addition, prepurification of antibody makes it possible to introduce $^{125}I$ into a higher proportion of specific antibody molecules (subclass of the IgG fraction), and thus more of the radioactive label is usable in the assay.

The purification procedure for antibody to be labeled involves known principles of affinity chromatography to an immunoglobulin cut of rabbit anti-serum to TSH. In a two-step procedure, the immunoglobulins are first passed over an HCG column to remove anti-alpha chain antibodies, and then over a TSH column. The specific anti-beta TSH antibodies bind to the TSH column, and they are eluted off in stages so that the final antibody for labeling consists of essentially pure anti-beta TSH antiboidies of high affinity. In addition to purification of the labeled antibody, the unlabeled antibody may be evaluated for TSH specificity and, if necessary, either passed over an HCG column prior to coupling to the solid phase support or absorbed with HCG after coupling to the solid phase support in order to provide a specific system. The assay utilizing these purified antibodies does not cross react with HCG, FSH, or LH at normal levels of these hormones, improving the specificity of the assay for TSH.

BRIEF DESCRIPTION OF THE DRAWINGS

The FIGURE shows a standard curve.

DESCRIPTION OF THE PREFERRED EMBODIMENT

The assay method of this invention can be applied to the assay of TSH in serum.

The reagents for a single-incubation two-site immunoradiometric assay for TSH are typically prepared as follows:

TRACER $^{125}I$-Antibody to Human Thyroid Stimulating Hormone

The antibodies to TSH are produced by injection of TSH into rabbits, according to usual procedures. They are purified according to the principles of affinity chromatography, above. The tracer is prepared by iodinating purified antibody with the isotope $^{125}I$ to a specific activity of about 1 to 100 $\mu Ci/\mu g$, preferably about 5 to 60 $\mu Ci/\mu g$. However, other specific activities may be used. The antibody may be iodinated by conventional methods described in the literature. The tracer may be lyophilized from a solution containing phosphate buffer and carrier protein.

SOLID-PHASE RECEPTOR

Antibody to Human Thyroid Stimulating Hormone Immobilized on Derivatized Polyacrylamide Beads The hydrolysis of polyacrylamide beads and the coupling of antibody to these beads is essentially as described in U.S. Pat. No. 4,088,746, although the hydrolysis may also be carried out at room temperature. The antibody which is coupled is preferably a globulin cut of the antiserum, although whole serum can be used. Usually from 0.25 to 2.0 ml of antibody is coupled to each gram of beads, preferably 0.75 to 1.5 ml per gram. The washing of the coupled beads is accomplished by use of phosphate buffer and 1M ammonium thiocyanate. The beads may be lyophilized from a solution containing phosphate buffer, protein, and HCG, although they can also be left in liquid suspension.

The solid-phase receptor is used at a concentration such that under the assay conditions, the precipitation of TSH is essentially complete. The amount used per assay tube is approximately 1.0 to 5.0 mg, although other amounts may be used.

STANDARDS

The standards contain human TSH in human serum-based solution. The serum is stripped of endogenous TSH by charcoal and filtration prior to use. Alternatively, the protein environment of serum may be simulated by the use of dissolved serum or other proteins from human or animal origin. Preferably preservatives are added to the serum, conveniently sodium azide at 0.1% by weight. The human TSH contained in the standards are calibrated against the international reference preparation of human TSH supplied by the World Health Organization (Medical Research Council, Holly Hill, London). However, other standardizations may be used. Preferably the standards are lyophilized and they may be prepared to contain 0, 2.5, 5.0, 10, 25, 50 and 100 $\mu IU/ml$ TSH, although other levels could be used.

The reaction parameters are typically as described below:

VOLUME

Reaction volumes are kept reasonably small, although larger volumes can be used and the concentrations adjusted accordingly. Typically, 50 $\mu l$ of tracer with about 50,000 to 300,000 dpm, preferably 100,000 to 200,000 dpm, is added to each assay tube. The volume of solid-phase receptor added to each tube may vary from about 100 $\mu l$ to 500 $\mu l$, preferably 150 $\mu l$ to 400 $\mu l$.

The tracer and solid-phase receptor are preferably mixed and a single addition step is employed, but they may be added in two steps with the solid-phase receptor added first.

INCUBATION CONDITIONS

The incubation temperature is preferably in the range of 2°–50° C., preferably 35°–40° C., the incubation time is conveniently as specified in Example 1, although times of from about one hour to about three hours could be used and acceptable standard curves obtained. Prior to incubation, mixing of the tubes is conveniently done with a laboratory Vortex mixer, although the tubes could also be mixed by manual agitation.

REAGENT PREPARATION

The tracer is conveniently supplied in lyophilized form, although liquid tracer could also be used and appears to give similar stability characteristics. The solid-phase receptor is conveniently bottled and supplied as a suspension, although lyophilized preparations of solid-phase receptor appear to work equally well. The amounts of tracer and solid-phase receptor in each vial are adjusted so that prior to the assay, one vial of tracer could be reconstituted and mixed with one vial of solid-phase receptor. Alternatively, the number of tubes in a particular assay could be determined, and the appropriate amounts of tracer and solid-phase receptor could be mixed in a separate vial prior to the assay. The standards are conveniently supplied in lyophilized form.

EXAMPLE 1

PREPARATION FOR ASSAY

Approximately thirty minutes before the assay is to be run:

1. Reconstitute $^{125}$I-antibody to human TSH (tracer) with 2.5 ml distilled water.
2. Reconstitute Zero Standard with 5.0 ml distilled water.
3. Reconstitute standards containing 2.5–100 µIU/ml human TSH with 2.0 ml distilled water.
4. Prepare a normal saline solution (0.9% or 0.154 molar sodium chloride) in distilled water and store at room temperature.
5. Prepare tracer-bead reagent by combining one vial of $^{125}$I-antibody with one vial of solid-phase receptor.

Each reagent must be thoroughly dissolved and mixed with the added water before use. All reagents and specimens should be allowed to come to room temperature before use. The tracer-bead reagent will be a fine suspension of polymeric particles and will appear cloudy. If more than 50 tubes are being run at one time, two vials of tracer should be reconstituted and mixed with two vials of solid-phase receptor in one vial, prior to use in the assay.

ASSAY PROTOCOL

1. Label sixteen tubes in duplicate as follows: TC, zero, 2.5, 5.0, 10, 25, 50, and 100 µIU/ml. Label two tubes in duplicate for each patient serum and sample and for each commercial control serum.
2. Add 200 µl Standards zero through 100 to the appropriate tubes.
3. Add 200 µl of each patient's serum or commercial control serum to the appropriate tubes.
4. Mix tracer-bead reagent thoroughly and add 200 µl to all tubes. Set aside TC tubes.
5. Vortex tubes and incubate for two hours at 37° C. (except TC tubes). This step comprises the single incubation mode or step of this invention.
6. Add 3.0 ml saline to all tubes (except TC) and centrifuge for 10 minutes at 1500×g. Immediately after the centrifuge has stopped, decant tubes and blot the tube against filter paper or plastic backed absorbent paper.
7. Count all tubes (including TC) for one minute.

RESULTS

The concentrations of human thyroid stimulating hormone in the patient's samples and commercial control serum are determined from a standard curve. Standard curves may be obtained by several methods, for example, by plotting cpm vs. concentration. FIG. 1 shows a sample standard curve where cpm is plotted vs. concentration. The standard curve must be constructed for each assay, as the actual numbers will vary with the age of the reagents.

Sample data generated using this assay are shown below. These numbers were used to plot the standard curve in FIG. 1.

| Sample | cpm | TSH Value |
|---|---|---|
| TC | 144062,143313 | |
| Zero | 6094,5464 | 0 µIU/ml |
| 2.5 µIU/ml Standard | 9318,9116 | 2.5 µIU/ml |
| 5.0 µIU/ml Standard | 11859,11745 | 5.0 µIU/ml |
| 10 µIU/ml Standard | 17992,15301 | 10 µIU/ml |
| 25 µIU/ml Standard | 25203,25241 | 25 µIU/ml |
| 50 µIU/ml Standard | 37266,35871 | 50 µIU/ml |
| 100 µIU/ml Standard | 49535,48363 | 100 µIU/ml |
| Commercial Control I | 13187,12766 | 6.2 µIU/ml |
| Commercial Control II | 19773,19413 | 14.9 µIU/ml |
| Commercial Control III | 24519,25028 | 23.5 µIU/ml |
| Patient 1 | 7009,6139 | 0.8 µIU/ml |
| Patient 2 | 23466,24102 | 21.6 µIU/ml |
| Patient 3 | 8373,7694 | 1.4 µIU/ml |

The major use of the present invention from a practical standpoint takes place in clinical laboratories. Typically such laboratories obtain commercial kits containing the various reagents required to perform the assay. Accordingly, the present invention contemplates kits for assaying a specimen for a multivalent ligand having improved reagents permitting the use of a single incubation mode as discussed above. Such kits will comprise containers of: (a) labeled receptor for said multivalent ligand; and (b) an unlabeled receptor for said multivalent ligand covalently bound to a solid-phase support which forms a substantially stable aqueous suspension. Usually the kits will also comprise containers of standards for the multivalent ligand to be assayed. The kits in general may also comprise containers having the various other reagents previously described including those utilized in the preferred embodiment.

We claim:

1. An improved two-site immunoassay method, which comprises:
   bringing together in an aqueous medium in an essentially single-incubation mode (a) the sample containing the multivalent ligand to be determined, (b) a labeled receptor for said ligand, and (c) an excess of unlabeled receptor to bind substantially all said ligand, said unlabeled receptor being covalently bound to a solid-phase support which forms a substantially stable suspension;

incubating said aqueous medium to produce a two-phase system, wherein the solid phase contains substantially all said ligand bound to both said unlabeled receptor and said labeled receptor, and the liquid phase contains the unbound portion of said labeled receptor;

separating said solid and liquid phases from each other; and analyzing either phase for the labeled receptor, being a function of the concentration of said ligand in said sample.

2. An improved two-site immunoassay method in accordance with claim 1, wherein said solid-phase support is derivatized polyacrylamide particles of about 0.1 to 10 microns in size.

3. An improved two-site immunoassay method in accordance with claim 1, wherein said ligand is human thyroid stimulating hormone and said receptors for said ligand are antibodies against human thyroid stimulating hormone.

4. An improved two-site immunoassay in accordance with claim 3, wherein said labeled antibody against human thyroid stimulating hormone has been prepurified and consists essentially of those species of antibody against thyroid stimulating hormone having relatively high affinity and specificity for human thyroid stimulating hormone.

5. An improved two-site immunoassay method in accordance with claim 3, wherein said labeled antibody against said human thyroid stimulating hormone is labeled with a tractor atom or molecule.

6. An improved two-site immunoassay method in accordance with claim 5, wherein said tracer is a radioactive atom or molecule.

7. An improved two-site immunoassay method in accordance with claim 6, wherein said tracer is radioactive iodine 125.

8. An improved two-site immunoradiometric assay method for human thyroid stimulating hormone which comprises:

bringing together in an aqueous medium in essentially a single-incubation mode (a) the sample containing said human thyroid stimulating hormone to be determined, (b) a radioactively labeled antibody against human thyroid stimulating hormone, and (c) an excess of said unlabeled antibody to bind substantially all said human thyroid stimulating hormone, said unlabeled antibody being covalently bound to derivatized polyacrylamide particles of about 0.1 to 10 microns in size which forms a substantially stable suspension;

incubating said aqueous medium to produce a two-phase system, wherein the solid phase contains substantially all said hormone bound to both said unlabeled antibody and said labeled antibody, and the liquid phase contains the unbound portion of said labeled antibody;

separating said solid and liquid phases from each other; and analyzing either phase for said labeled antibody, being a function of the concentration of sais hormone in said sample.

9. An improved two-site immunoradiometric assay according to claim 8, wherein said labeled antibody has been prepurified and consists essentially of those species of antibody having relatively high affinity and specificity for human thyroid stimulating hormone.

10. An improved two-site immunoradiometric assay according to claim 8, wherein said labeled antibody is labeled with radioactive iodine 125.

11. In an assay kit for assaying a specimen for a multivalent ligand, improved reagents permitting the use of a single incubation mode in the assay comprising containers of: (a) a labeled receptor for said multivalent ligand; and (b) an excess of unlabeled receptor to bind substantially all said multivalent ligand, said unlabeled receptor covalently bound to a solid-phase support which forms a substantially stable aqueous suspension.

12. The improved assay kit in accordance with claim 11 wherein said kit includes containers of standards for the multivalent ligand to be assayed.

13. The improved assay kit in accordance with claim 11 wherein said solid-phase support is derivatized polyacrylamide particles of about 0.1 to 10 microns in size.

14. The improved assay kit in accordance with claim 13 wherein said ligand is human thyroid stimulating hormone and said receptors for said ligand are antibodies against human thyroid stimulating hormone.

15. The improved assay kit in accordance with claim 14 wherein said labeled antibody against human thyroid stimulating hormone has been prepurified and consists essentially of those species of antibody against thyroid stimulating hormone having relatively high affinity and specificity for human thyroid stimulating hormone.

16. The improved assay kit in accordance with claim 14 wherein said labeled antibody against said human thyroid stimulating hormone is labeled with a tracer atom or molecule.

17. The improved assay kit in accordance with claim 16 wherein said tracer is a radioactive atom or molecule.

18. The improved assay kit in accordance with claim 17 wherein said tracer is radioactive iodine 125.

19. An improved two-site immunoassay method in accordance with claim 1, further comprising mixing together said excess of unlabeled receptor and said labeled receptor prior to said step of bringing together.

20. An improved two-site immunoradiometric assay method in accordance with claim 8, further comprising mixing together said excess of unlabeled antibody and said radioactively labeled antibody prior to said step of bringing together.

* * * * *